(12) United States Patent
Mori et al.

(10) Patent No.: US 10,702,210 B2
(45) Date of Patent: Jul. 7, 2020

(54) MEAL INTAKE DETECTION DEVICE, MEAL INTAKE DETECTION METHOD AND COMPUTER-READABLE NON-TRANSITORY MEDIUM

(71) Applicant: FUJITSU LIMITED, Kawasaki-shi, Kanagawa (JP)

(72) Inventors: Tatsuya Mori, Sagamihara (JP); Kazuho Maeda, Kawasaki (JP); Akihiro Inomata, London (GB)

(73) Assignee: FUJITSU LIMITED, Kawasaki (JP)

( * ) Notice: Subject to any disclaimer, the term of this patent is extended or adjusted under 35 U.S.C. 154(b) by 79 days.

(21) Appl. No.: 15/969,021

(22) Filed: May 2, 2018

(65) Prior Publication Data

US 2018/0242909 A1    Aug. 30, 2018

Related U.S. Application Data

(63) Continuation of application No. PCT/JP2015/081122, filed on Nov. 5, 2015.

(51) Int. Cl.
*A61B 5/00*    (2006.01)
*A61B 5/024*    (2006.01)
*G16H 50/20*    (2018.01)
*G16H 20/60*    (2018.01)

(52) U.S. Cl.
CPC ........ *A61B 5/4866* (2013.01); *A61B 5/02405* (2013.01); *A61B 5/02438* (2013.01); *A61B 5/7278* (2013.01); *A61B 5/7282* (2013.01); *G16H 20/60* (2018.01); *G16H 50/20* (2018.01)

(58) Field of Classification Search
CPC .............................. A61B 5/4866; G16H 50/20

USPC .......................................................... 600/508
See application file for complete search history.

(56) References Cited

U.S. PATENT DOCUMENTS

| | | | |
|---|---|---|---|
| 5,398,688 A | 3/1995 | Laniado | |
| 2010/0174153 A1* | 7/2010 | Nakagawa | G16H 40/63 600/301 |

FOREIGN PATENT DOCUMENTS

| | | |
|---|---|---|
| EP | 3 231 362 A1 | 10/2017 |
| JP | 10-504739 | 5/1998 |
| JP | 2000-245713 | 9/2000 |
| JP | 2003-173375 | 6/2003 |

(Continued)

OTHER PUBLICATIONS

Extended European Search Report dated Oct. 4, 2018 from European Patent Application No. 15907801.3, 10 pages.

(Continued)

*Primary Examiner* — Nadia A Mahmood
(74) *Attorney, Agent, or Firm* — Staas & Halsey LLP

(57) ABSTRACT

A meal intake detection device includes: a memory; and a processor coupled to the memory and configured to: detect a rise of heart rate; extract as a meal intake candidate a time range from a detected rise to time when the heart rate decreases to a predetermined value in temporal changes in heart rate, and when a second meal intake candidate is extracted in a time range of an extracted first meal intake candidate, separate the first meal intake candidate and the second meal intake candidate along a predetermined line; and detect whether each of the first meal intake candidate and the second meal intake candidate is a meal intake based on feature quantities relating to the first meal intake candidate and the second meal intake candidate that are separated.

6 Claims, 14 Drawing Sheets

(56) References Cited

FOREIGN PATENT DOCUMENTS

| JP | 2005-21450 | 1/2005 |
|----|------------|--------|
| JP | 2010-158267 | 7/2010 |
| JP | 2011-115508 | 6/2011 |
| JP | 2012-61790 | 3/2012 |

OTHER PUBLICATIONS

Ouchi et al., "LifeMinder: A Wearable Healthcare Support System with Timely Instruction Based on the User's Context", Advanced Motion Control, 2004 8th IEEE International Workshop, pp. 445-450, Mar. 25, 2004.
Amft et al., "On-Body Sensing Solutions for Automatic Dietary Monitoring", IEEE Pervasive Computing, IEEE Service Center, vol. 8, No. 2, pp. 62-70, Apr. 1, 2009.
International Search Report dated Jan. 19, 2016 in corresponding International Application No. PCT/JP2015/081122, 3 pages.
Written Opinion dated Jan. 19, 2016 in corresponding International Application No. PCT/JP2015/081122, 4 pages.
Kazushige Ouchi et al., "Healthcare Services Using a Wearable Device", IPSJ SIG Technical Report, Feb. 23, 2007, vol. 2007, No. 14, pp. 29-36**.

* cited by examiner

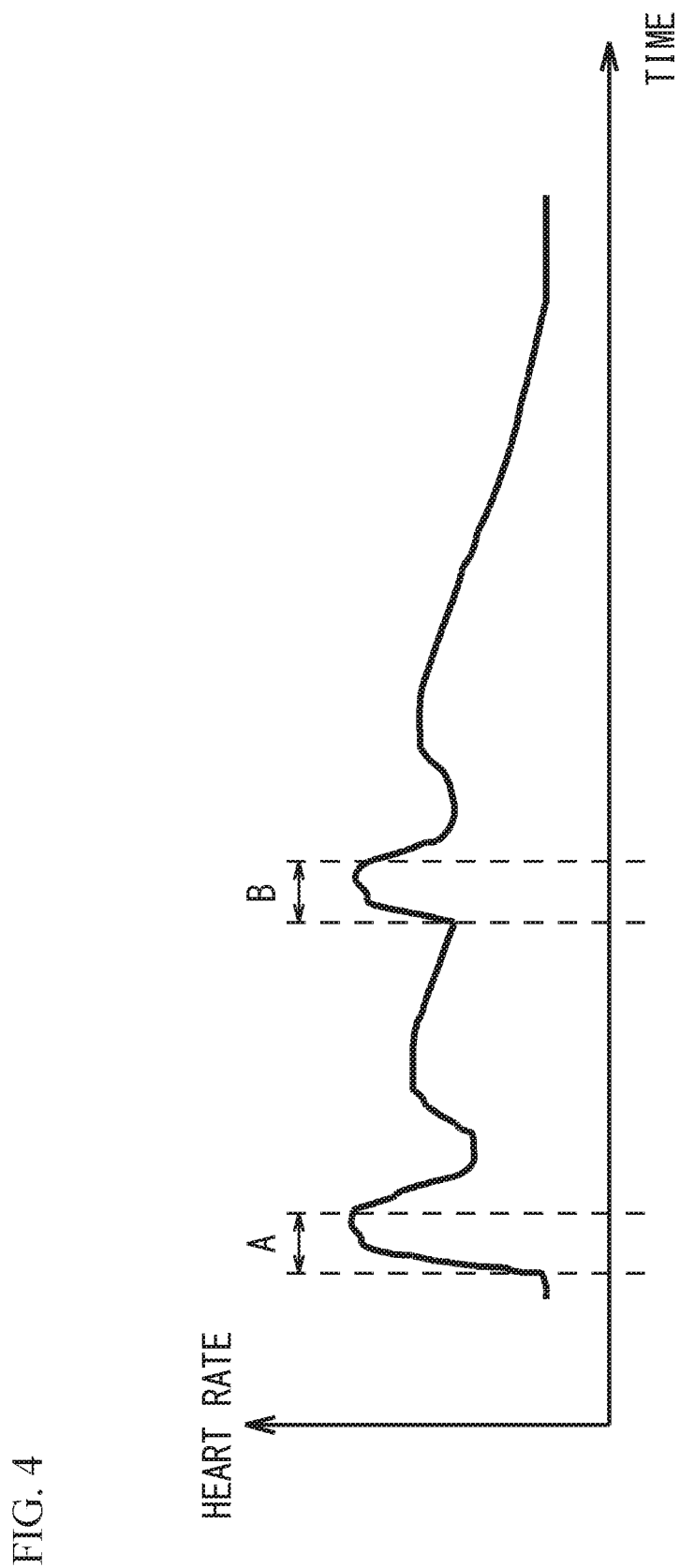

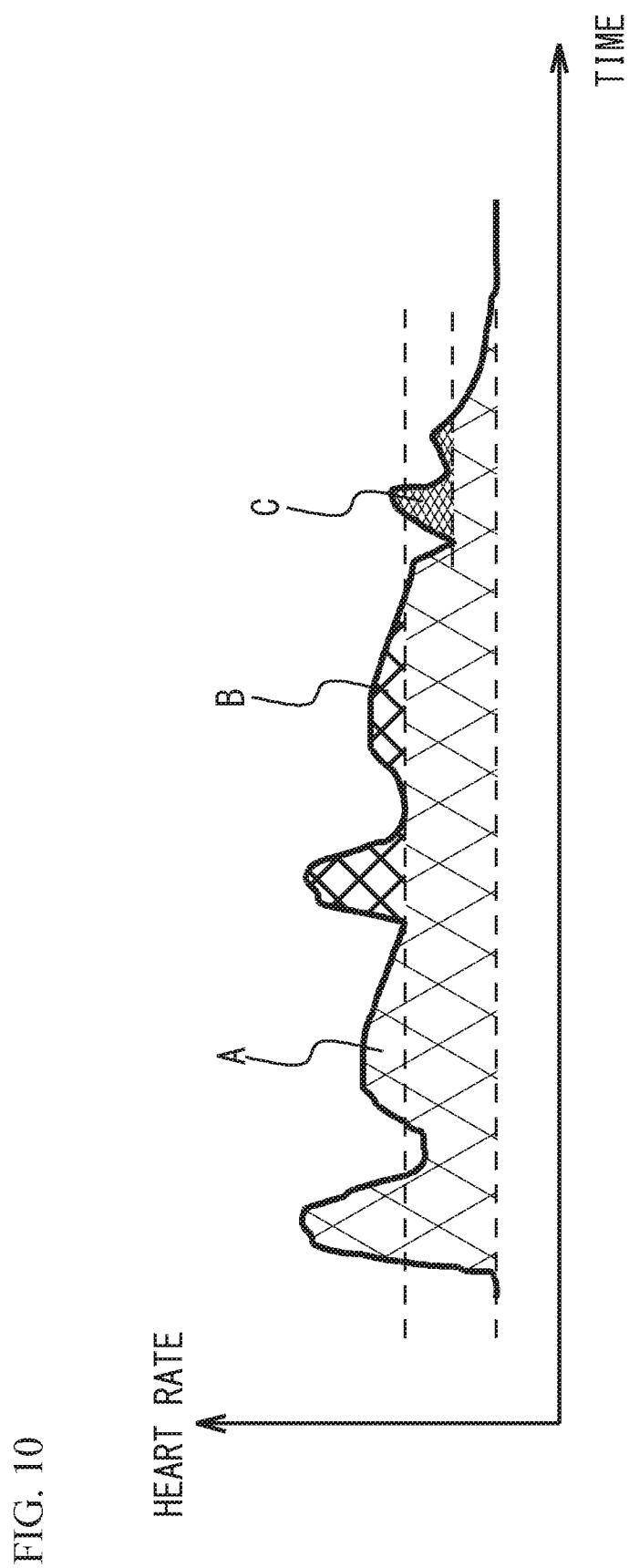

MEAL INTAKE DETECTION DEVICE, MEAL INTAKE DETECTION METHOD AND COMPUTER-READABLE NON-TRANSITORY MEDIUM

CROSS-REFERENCE TO RELATED APPLICATIONS

This application is a continuation application of International Application PCT/JP2015/081122 filed on Nov. 5, 2015 and designated the U.S., the entire contents of which are incorporated herein by reference.

FIELD

A certain aspect of the embodiments discussed herein is related to a meal intake detection device, a meal intake detection method, and a non-transitory computer-readable storage medium.

BACKGROUND

A technique for detecting a meal intake has been desired. For example, Japanese Laid-open Patent Publication No. 2010-158267 discloses a technique that detects temporal changes in heart rate and determines the peak of the heart rate satisfying a predetermined condition as a meal intake.

SUMMARY

According to an aspect of the present invention, there is provided a meal intake detection device including: a memory; and a processor coupled to the memory and configured to: detect a rise of heart rate; extract as a meal intake candidate a time range from a detected rise to time when the heart rate decreases to a predetermined value in temporal changes in heart rate, and when a second meal intake candidate is extracted in a time range of an extracted first meal intake candidate, separate the first meal intake candidate and the second meal intake candidate along a predetermined line; and detect whether each of the first meal intake candidate and the second meal intake candidate is a meal intake based on feature quantities relating to the first meal intake candidate and the second meal intake candidate that are separated.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 4 illustrates detection of meal intake candidates;

FIG. 10 illustrates meal intake candidates;

DESCRIPTION OF EMBODIMENTS

When peaks of the heart rate overlap because of a short interval between meals, the accuracy of the detection of a meal intake may decrease.

Hereinafter, a description will be given of embodiments with reference to drawings.

First Embodiment

Figure 1:
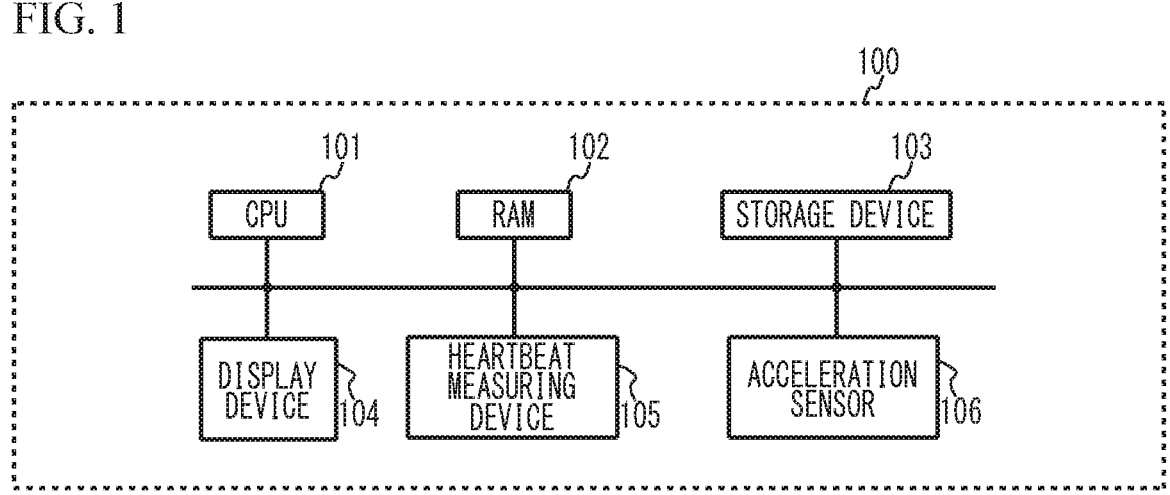
FIG. 1 is a block diagram of a hardware configuration of a meal intake detection device in accordance with a first embodiment.

FIG. 1 is a block diagram of a hardware configuration of a meal intake detection device 100 in accordance with a first embodiment. As illustrated in FIG. 1, the meal intake detection device 100 includes a CPU 101, a RAM 102, a storage device 103, a display device 104, a heartbeat measuring device 105, an acceleration sensor 106, and the like. These devices are interconnected through a bus or the like.

The CPU (Central Processing Unit) 101 is a central processing unit. The CPU 101 includes one or more cores. The RAM (Random Access Memory) 102 is a volatile memory that temporarily stores programs executed by the CPU 101 and data processed by the CPU 101.

The storage device 103 is a nonvolatile storage device. For example, a ROM (Read Only Memory), a solid state drive (SSD) such as a flash memory, or a hard disk driven by a hard disk drive can be used as the storage device 103. The meal intake detection program of the present embodiment is stored in the storage device 103. The display device 104 is a liquid crystal display, an electroluminescence panel, or the like, and displays the result of the meal intake detection process described later.

The heartbeat measuring device 105 is a device that measures the heartbeat (pulse) of a user. The heartbeat measuring device 105 is not particularly limited as long as it can measure heartbeat (pulse). For example, the heartbeat measuring device 105 may be an electrocardiograph or a pulsation sensor. The acceleration sensor 106 is a sensor that detects an acceleration of a part to which the sensor is attached of the user.

The meal intake detection program stored in the storage device 103 is deployed in the RAM 102 in an executable manner. The CPU 101 executes the meal intake detection program deployed in the RAM 102. This causes the meal intake detection device 100 to execute each process. FIG.

2A is a block diagram of functions implemented by the execution of the meal intake detection program. The execution of the meal intake detection program implements a heart rate acquisition unit 10, a meal intake candidate detection unit 20, a heartbeat peak extraction unit 30, a heartbeat peak correction unit 40, an acceleration acquisition unit 50, an action detection unit 60, a meal intake detection unit 70, a meal index estimation unit 80, and the like.

Figure 2A:
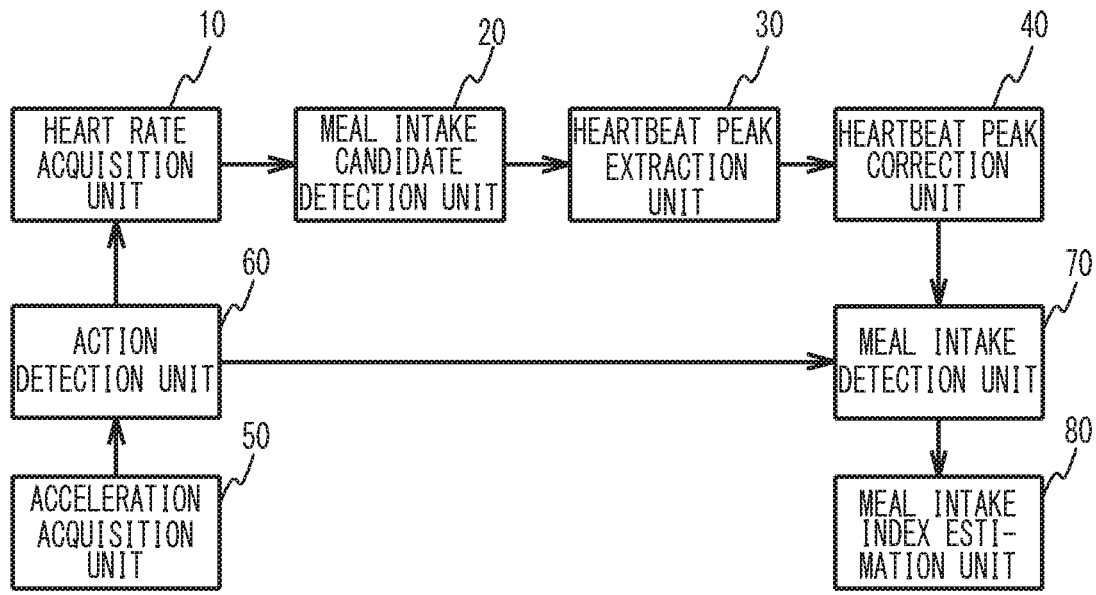
FIG. 2A is a block diagram of functions implemented by the execution of a meal intake detection program.
Figure 2B:
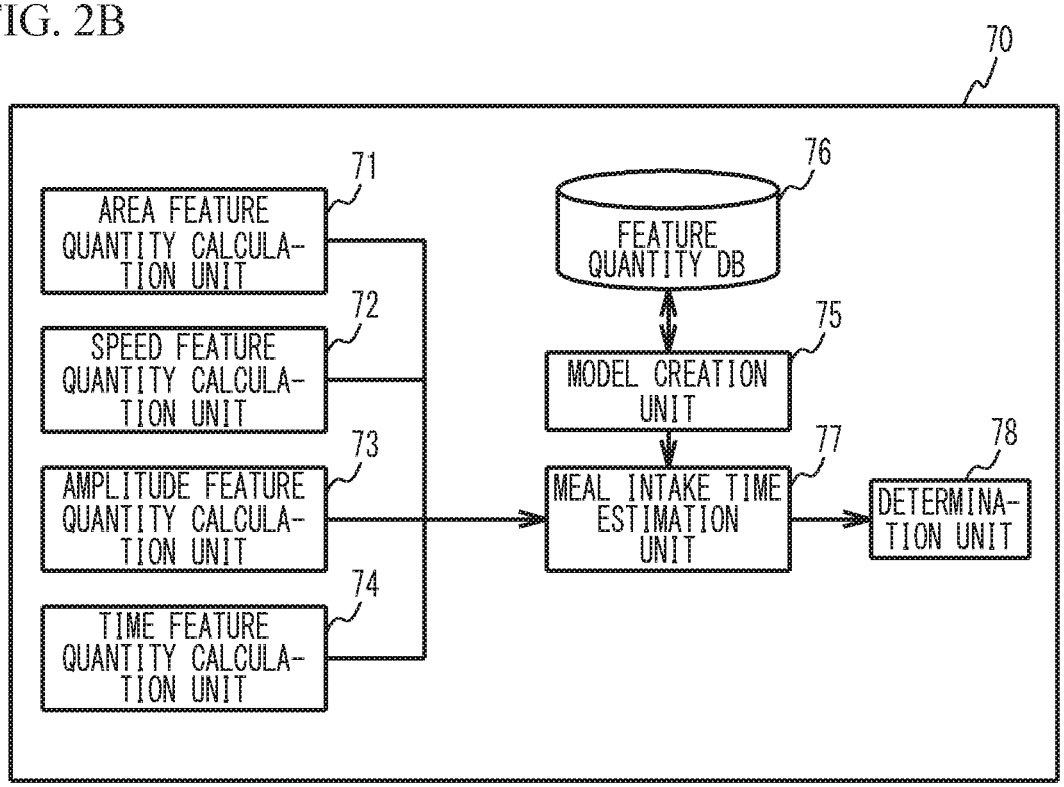
FIG. 2B is a functional block diagram of functions of a meal intake detection unit.

FIG. 2B is a functional block diagram of functions of the meal intake detection unit 70. As illustrated in FIG. 2B, the meal intake detection unit 70 functions as an area feature quantity calculation unit 71, a speed feature quantity calculation unit 72, an amplitude feature quantity calculation unit 73, a time feature quantity calculation unit 74, a model creation unit 75, a feature quantity database 76, a meal intake time estimation unit 77, a determination unit 78, and the like.

Figure 3A:
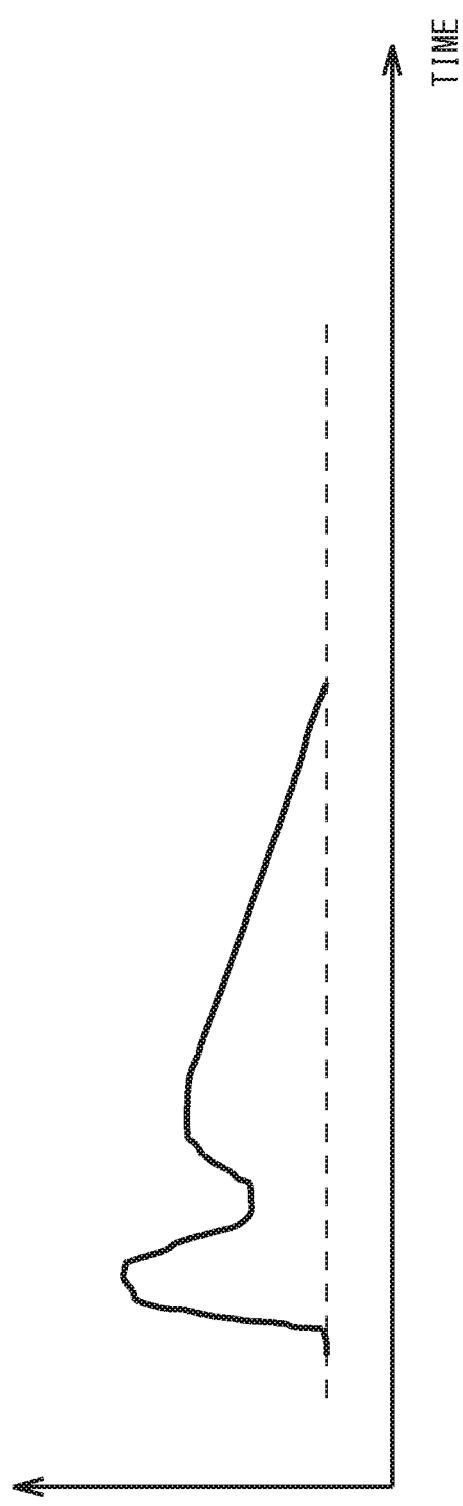
FIG. 3A illustrates temporal changes in heart rate during a meal.

Here, a description will be given of temporal changes in heart rate resulting from a meal intake. FIG. 3A illustrates temporal changes in heart rate resulting from a meal intake. In FIG. 3A, the horizontal axis represents elapsed time, and the vertical axis represents heart rate. The heart rate is the number of beats per unit time, more specifically, the number of beats per minute. Hereinafter, unless otherwise specified, the heart rate means the number of beats per minute.

As illustrated in FIG. 3A, two peaks appear in the heart rate increase section occurring with a meal intake. The start point of the increase section where the rise of the first peak is detected is a meal intake start time. For example, the start point at which the ascent rate of the heart rate is equal to or greater than a threshold value and the rise in heart rate is equal to or greater than another threshold value can be detected as the rise. The time of the first peak is a meal intake end time. The time when the heart rate of the second peak has returned to a predetermined value is the end point of the heart rate increase section. For example, the time when the heart rate of the second peak returns to the heart rate at the meal intake start time may be defined as the end point of the heart rate increase section, or time when the heart rate of the second peak returns to the value calculated by adding a predetermined value to the heart rate at the meal intake start time or multiplying the heart rate at the meal intake start time by the predetermined value may be defined as the end point of the heart rate increase section. The waveform of the heart rate from the start point to the end point of the heart rate increase section occurring with a meal intake is referred to as a heartbeat peak.

Figure 3B:
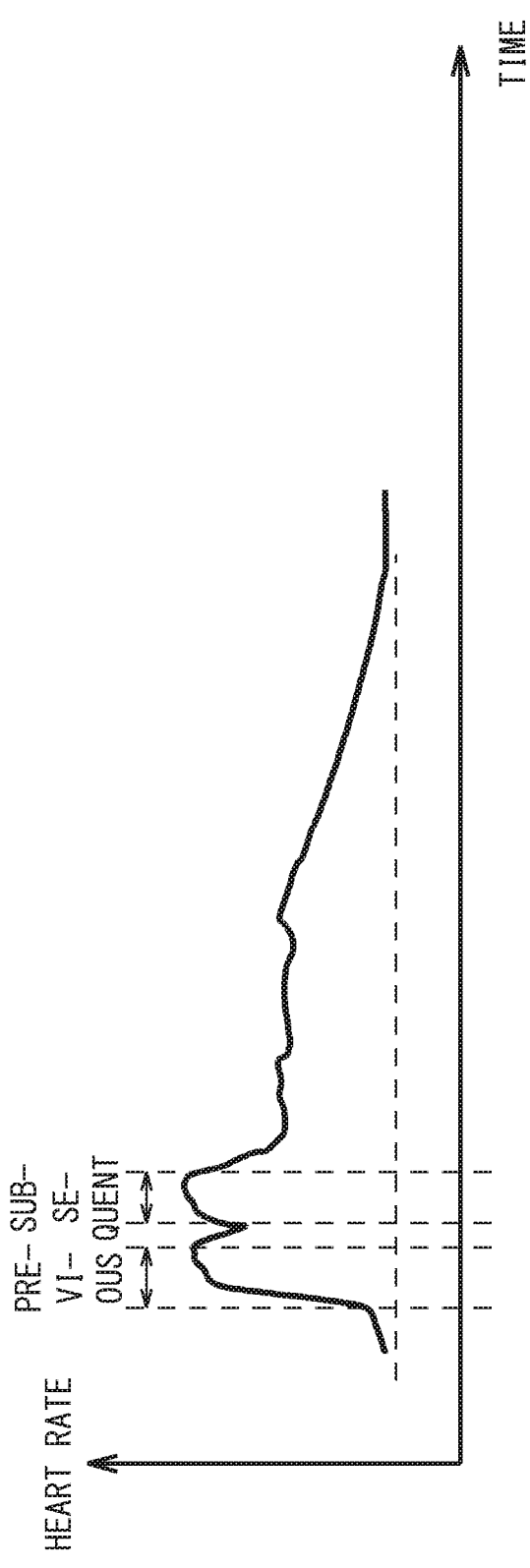
FIG. 3B illustrates temporal changes in heart rate when the interval between meals is short.

Meal intakes at predetermined intervals allow heartbeat peaks illustrated in FIG. 3 to be sufficiently separated and detected. Thus, a meal intake can be accurately detected. However, when the interval between meals is short, as illustrated in FIG. 3B, heartbeat peaks overlap with each other. In the example of FIG. 3B, following the first peak in the previous meal, the second peak in the subsequent meal appears. In this case, the accuracy of the detection of a meal intake decreases. Thus, the present embodiment describes an example that improves the accuracy of the detection of a meal intake by detecting heartbeat peak candidates, and extracting individual heartbeat peaks.

(Meal Intake Detection Process)

First, the acceleration acquisition unit 50 acquires the detection result of the acceleration sensor 106. When the acceleration of the user satisfies a predetermined condition, this indicates that the user is exercising, such as running, walking, or the like. Thus, the action detection unit 60 detects the exercise interval of the user based on the detection results acquired by the acceleration acquisition unit 50.

The heart rate acquisition unit 10 acquires temporal changes in heart rate by acquiring heartbeat from the heartbeat measuring device 105. The heart rate acquisition unit 10 then eliminates the variation in heart rate during the exercise interval. This process eliminates as a noise the exercise interval during which it is estimated that the user is not having a meal.

Then, the meal intake candidate detection unit 20 detects meal intake candidates from the temporal changes in heart rate. In the present embodiment, when the rise at which the degree of increase in heart rate per unit time (the ascent rate of the heart rate) is equal to or greater than a threshold value is detected, the meal intake candidate detection unit 20 detects the period after the rise as a meal intake candidate. The detection condition may be looser than the detection condition by the meal intake detection unit 70 so that the actual meal intake can be reliably detected. For example, when the section in which the ascent rate of heart rate within 20 minutes from the rise of the heart rate to the maximum point is 10/min or greater is detected, the meal intake candidate detection unit 20 detects the period after the rise as a meal intake candidate. In the example of FIG. 4, two candidates including a first meal intake candidate A and a second meal intake candidate B are detected.

Figure 5:
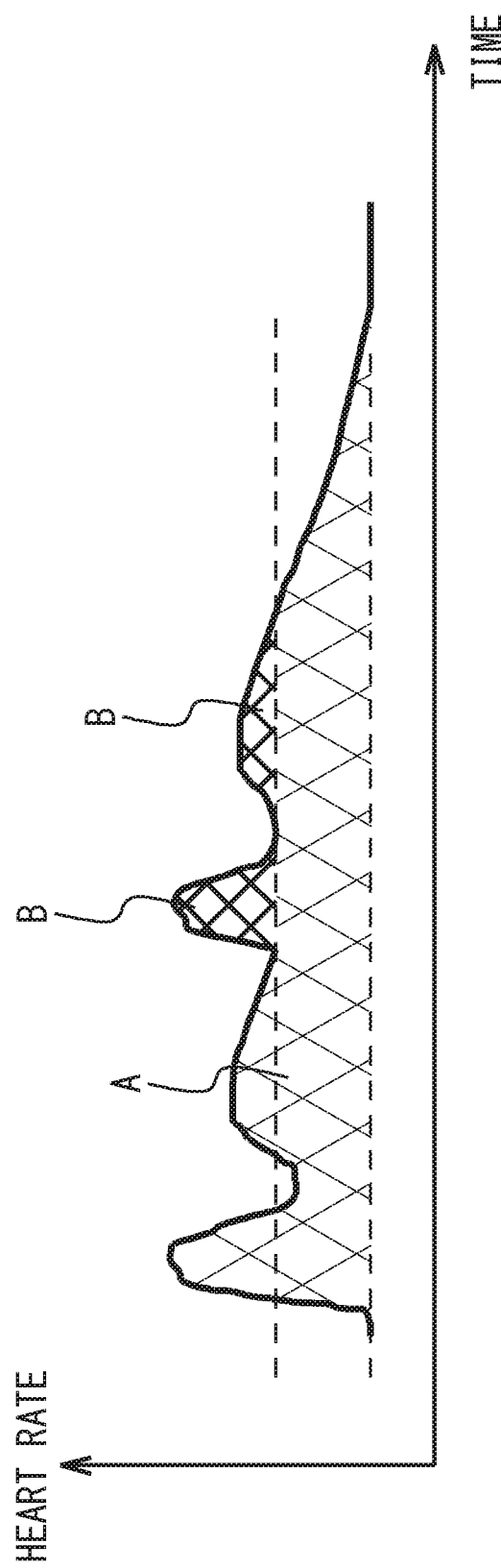
FIG. 5 illustrates separation of meal intake candidates.

The heartbeat peak extraction unit 30 then extracts the heartbeat peak of each meal intake candidate. In the present embodiment, as an example, the heartbeat peak extraction unit 30 detects the rise of the heart rate as the start point of the heartbeat peak of the meal intake candidate, and detects, as the end point of the heartbeat peak of the meal intake candidate, the time when the heart rate returns to the heart rate at the meal intake start time. As illustrated in FIG. 5, the heartbeat peaks of the first meal intake candidate A and the second meal intake candidate B are detected in a manner that the heartbeat peak of the second meal intake candidate B is added to the heartbeat peak of the first meal intake candidate A.

The heartbeat peak extraction unit 30 then extracts heartbeat peaks overlapping with each other as a collection of meal intake candidates. For example, when the time ranges of heartbeat peaks overlap, the heartbeat peak extraction unit 30 determines that the heartbeat peaks overlap. Then, the heartbeat peak extraction unit 30 separates the waveform of the overlapping heartbeat peaks into individual heartbeat peaks along a predetermined line by drawing the predetermined line in the waveform. For example, the period from the start point of the subsequent heartbeat peak to the time at which the heart rate returns to the heart rate at the start point may be set as the subsequent heartbeat peak and separated from the previous heartbeat peak. Alternatively, at the start point of the subsequent heartbeat peak, the subsequent heartbeat peak may be separated from the previous heartbeat peak.

Figure 6A:
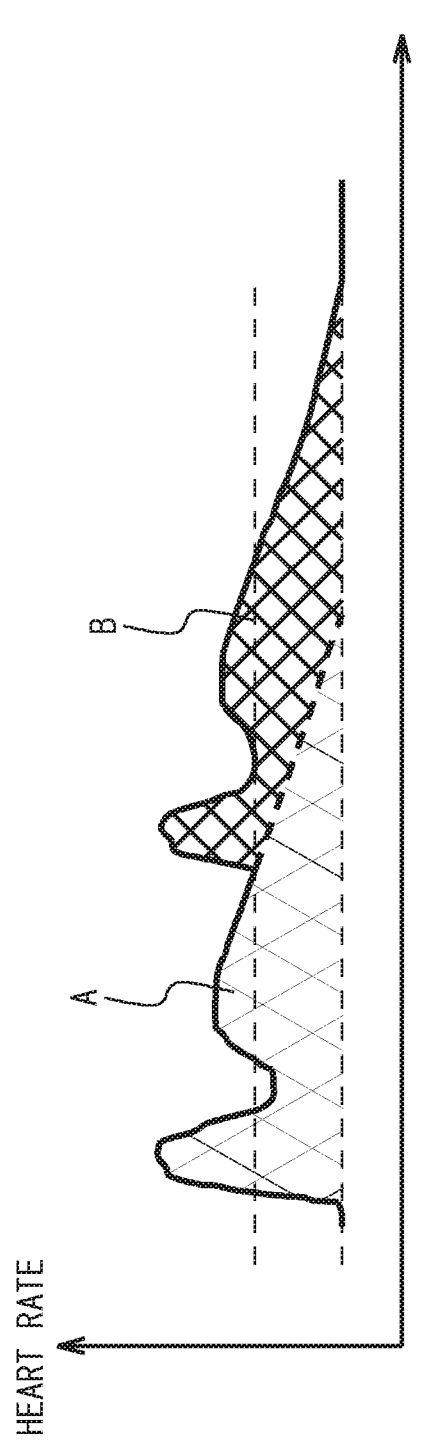
FIG. 6A through FIG. 6C illustrate correction of meal intake candidates.
Figure 6C:
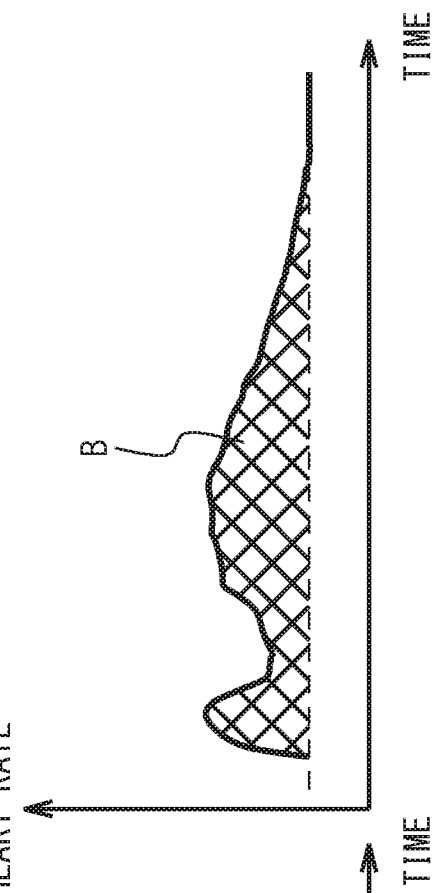
Figure 6B:
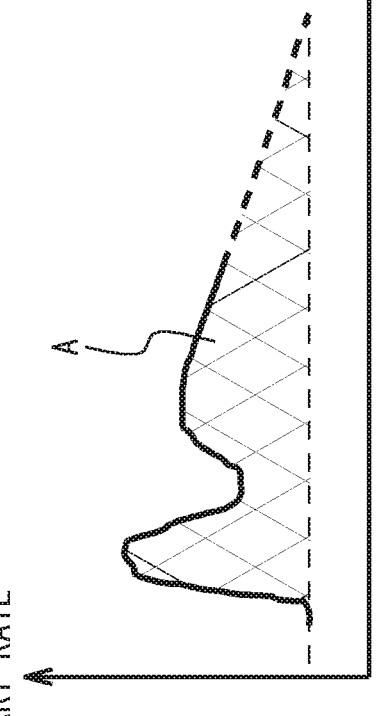

Then, the heartbeat peak correction unit 40 corrects the heartbeat peaks overlapping with each other. In the present embodiment, the heartbeat peak correction unit 40 corrects the previous and subsequent heartbeat peaks by using the previous heartbeat peak to the start point of the subsequent heartbeat peak. For example, it is assumed that the speed at which the rise in heartbeat accompanying with a meal intake comes close to the original level before the start of the meal intake is constant after the start time of the subsequent meal intake candidate. More specifically, the heartbeat peak correction unit 40 corrects the previous and subsequent heartbeat peaks by drawing a line from the start point of the subsequent meal intake candidate, the line having a slope equal to the slope of the heartbeat peak of the previous meal intake candidate. The dashed line in FIG. 6A illustrates a line for correcting the previous and subsequent heartbeat peaks. FIG. 6B illustrates a corrected previous heartbeat peak. FIG. 6C illustrates a corrected subsequent heartbeat peak.

Figure 7A:
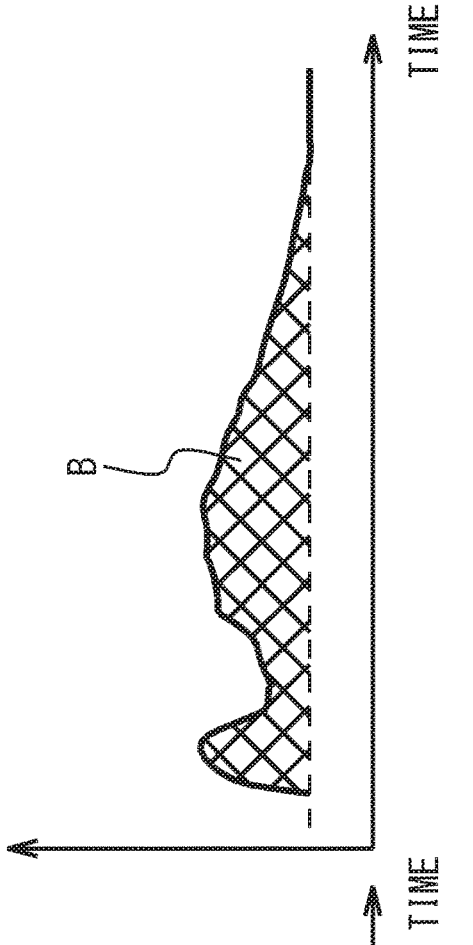
FIG. 7A and FIG. 7B illustrate calculation of a feature vector.
Figure 7B:
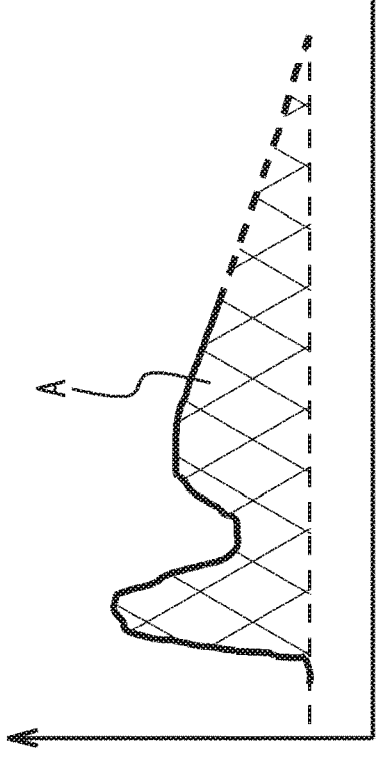

Then, the meal intake detection unit 70 calculates the feature vector based on each corrected heartbeat peak by the heartbeat peak correction unit 40 as illustrated in FIG. 7A and FIG. 7B. First, the area feature quantity calculation unit 71 calculates the area of each of the first peak and the second peak of the heartbeat peaks. For example, the area from the meal intake start time to the fall through the peak can be calculated as the area of the first peak. Similarly, the area from the rise after the first peak to the end of the meal through the peak can be calculated as the area of the second peak.

The speed feature quantity calculation unit 72 calculates a response speed of the heart rate. For example, the speed feature quantity calculation unit 72 calculates the ascent rate from the meal intake start time to the first peak, the descent rate from the first peak to the next rise, the ascent rate from the rise to the second peak, and the descent rate from the second peak to the end of the meal.

Then, the amplitude feature quantity calculation unit 73 calculates the heart rate of the first peak and the heart rate of the second peak as amplitude values. Then, the time feature quantity calculation unit 74 calculates the time from the start of the meal to the first peak, the time from the start of the meal to the second peak, and the time from the start of the meal to the end of the meal.

The above-described feature vector is a vector including at least one of the feature quantities calculated by the area feature quantity calculation unit 71, the speed feature quantity calculation unit 72, the amplitude feature quantity calculation unit 73, and the time feature quantity calculation unit 74. The feature vector may include a pre-meal feature quantity. For example, the feature vector may include a pre-meal feature quantity such as the area from the start of the meal to the time a predetermined time before the start of the meal or the heart rate at the meal intake start time. As the area from the start of the meal to the time a predetermined time before the start of the meal, the area of the heart rate between the time a predetermined time before the start of the meal and the meal intake start time may be used.

The feature quantity database 76 stores in advance as feature vectors the feature quantities calculated by using the changes in heart rate of one or more users who actually had a meal. The model creation unit 75 creates an estimation model based on the feature vectors stored in the feature quantity database 76. The meal time estimation unit 77 estimates a meal time by applying the estimation model to the calculated feature vector. The determination unit 78 determines whether the subject meal intake candidate is a meal intake according to the estimation result of the meal time estimation unit 77. The determination unit 78 may reflect the matching result between a meal intake action detected by the action detection unit 60 based on the detection result of the acceleration sensor 106 and a meal intake action pattern. When the meal intake action detected by the action detection unit 60 is distant from (is not similar to) the meal intake action pattern, it may be determined that the subject meal intake candidate is not a meal intake.

The meal index estimation unit 80 then estimates indexes relating to a meal intake by using the feature vector of the heartbeat peak determined as a meal intake by the determination unit 78. The indexes relating to a meal intake include a condition of a human, an eating action, calories, and the like. The index relating to a meal intake can be expressed as a function of the feature vector, and thus the index relating to a meal intake can be expressed as f(x) wherein x represents the feature vector. As an example, when calories are used as the index relating to a meal intake, the area of the second peak calculated by the area feature quantity calculation unit 71 can be used as x. Alternatively, after the feature vector is calculated based on the heartbeat peaks determined as meal intakes, the index relating to meal intakes may be estimated. For example, when y represents the feature vector calculated based on two heartbeat peaks determined as meal intakes, the index relating to a meal intake can be expressed as g(y). As an example, presented is a case where the index indicating an excessively short interval between meals is calculated. When the feature vector y includes two scalar values y1 and y2, the area of the second peak of the previous meal is represented by y1, and the area after the start time of the subsequent meal in the second peak is represented by y2, g(y) can be expressed by y2/y1.

Figure 8:
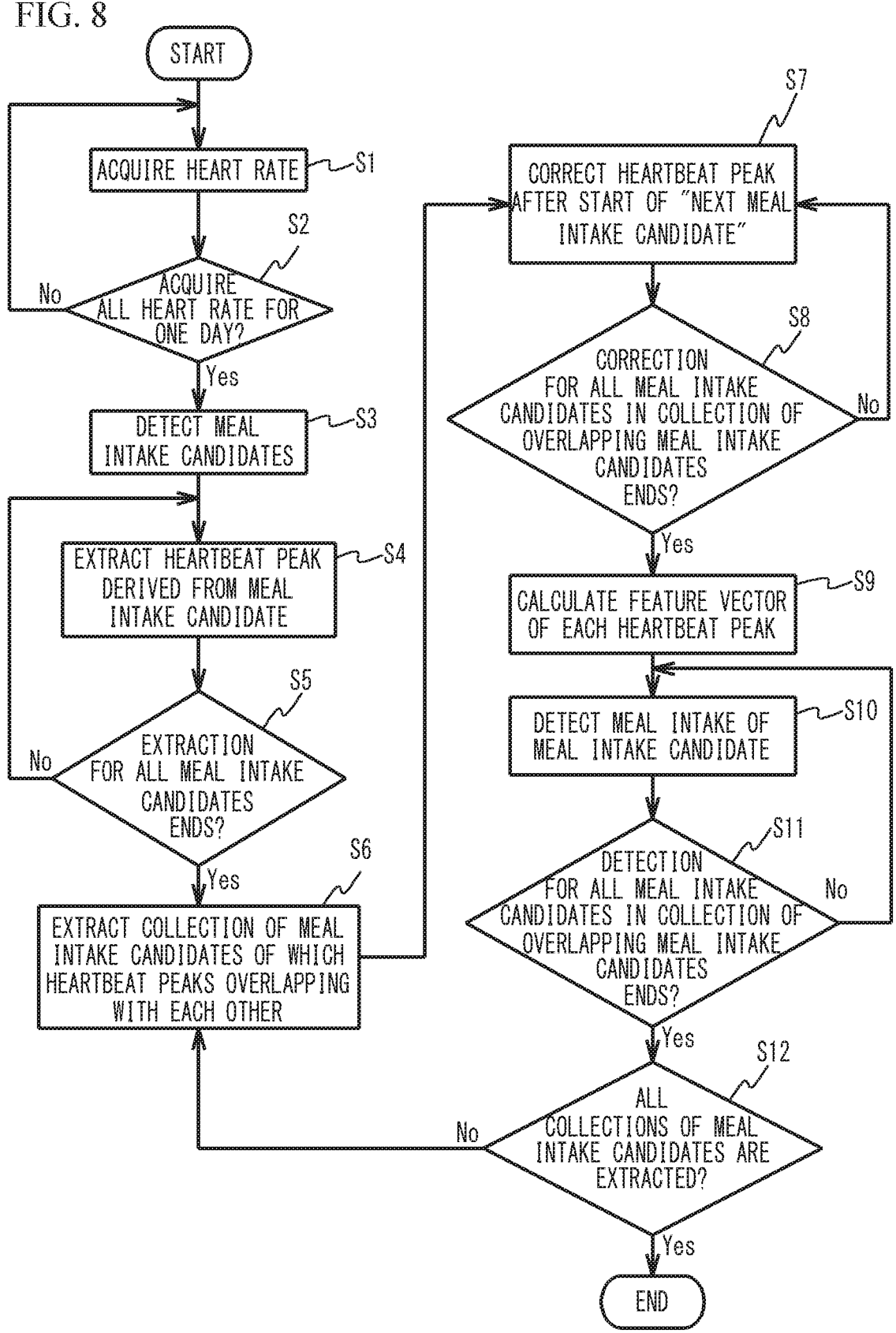
FIG. 8 is a flowchart of a concrete example of a meal intake detection process.

FIG. 8 is a flowchart of a concrete example of the above-described meal intake detection process. Hereinafter, the concrete example of the above-described meal intake detection process will be described along the flowchart of FIG. 8. As illustrated in FIG. 8, the heart rate acquisition unit 10 acquires the heart rate by using the heartbeat obtained from the heartbeat measuring device 105 (step S1). Then, the heart rate acquisition unit 10 determines whether it has acquired all the heart rate for one day (step S2). When the determination at step S2 is "No", the process is executed again from step S1.

When the determination at step S2 is "Yes", the meal intake candidate detection unit 20 detects meal intake candidates from temporal changes in heart rate (step S3). The heart rate acquisition unit 10 may eliminates as a noise the variation in heart rate during the exercise interval of the user detected by the action detection unit 60 before the execution of step S3. The heartbeat peak extraction unit 30 then extracts the heartbeat peak of each meal intake candidate (step S4). The heartbeat peak extraction unit 30 then determines whether the heartbeat peak is extracted for all the meal intake candidates (step S5). When the determination at step S5 is "No", the process is executed again from step S4.

When the determination at step S5 is "Yes", the heartbeat peak extraction unit 30 extracts the heartbeat peaks overlapping with each other as a collection of meal intake candidates (step S6). Then, the heartbeat peak correction unit 40 corrects the heartbeat peak after the start of the next meal intake candidate (step S7). At the first execution of step S7, the heartbeat peak after the start of the second meal intake candidate is corrected. Then, the heartbeat peak extraction unit 30 determines whether correction for all the meal intake candidates in the collection of overlapping meal intake candidates ends (step S8). When the determination at step S8 is "No", step S7 is executed again.

When the determination at step S8 is "Yes", the meal intake detection unit 70 calculates the feature vector based on each corrected heartbeat peak by the heartbeat peak correction unit 40 (step S9). Then, the meal intake detection unit 70 determines whether each meal intake candidate is a meal intake (step S10). Then, the meal intake detection unit 70 determines whether the determination is conducted to all the meal intake candidates in the collection of overlapping meal intake candidates (step S11). When the determination at step S11 is "No", step S10 is executed again. When the determination at step S11 is "Yes", the heartbeat peak extraction unit 30 determines whether all the collections of overlapping meal intake candidates are extracted (step S12).

When the determination at step S12 is "No", the process is executed again from step S6. When the determination at step S12 is "Yes", the execution of the flowchart ends.

In the present embodiment, the rise at which the ascent rate of the heart rate is equal to or greater than a threshold value in temporal changes in heart rate is detected. In the temporal changes in heart rate, the time range from the detected rise to the time at which the heart rate decreases to a predetermined value is extracted as a meal intake candidate. Among a plurality of meal intake candidates, when the second meal intake candidate is extracted in the time range of the first meal intake candidate, the first meal intake candidate and the second meal intake candidate are separated along a predetermined line. Based on the feature quantities relating to a meal intake of the separated first meal intake candidate and the separated second meal intake candidate, each of the first meal intake candidate and the second meal intake candidate is determined whether it is a meal intake. This configuration allows the meal intake detection based on the feature quantity for each meal intake candidate. This improves the accuracy of the detection of a meal intake.

The accuracy of the extraction of the first meal intake candidate and the second meal intake candidate is improved by obtaining the above-described predetermined line by using the first meal intake candidate to the start point of the second meal intake candidate. This is because the tendency of the first meal intake candidate can be used. When the heart rate of the first meal intake candidate tends to decrease at the time of the rising of the second meal intake candidate, a line that starts from the time of the rising of the second meal intake candidate and has a slope equal to that of the first meal intake candidate at the time of the rising of the second meal intake candidate is preferably obtained as the above-described predetermined line. When the heart rate of the first meal intake candidate tends to decrease, the heart rate tends to decrease at a constant rate.

Second Embodiment

Figure 9A:
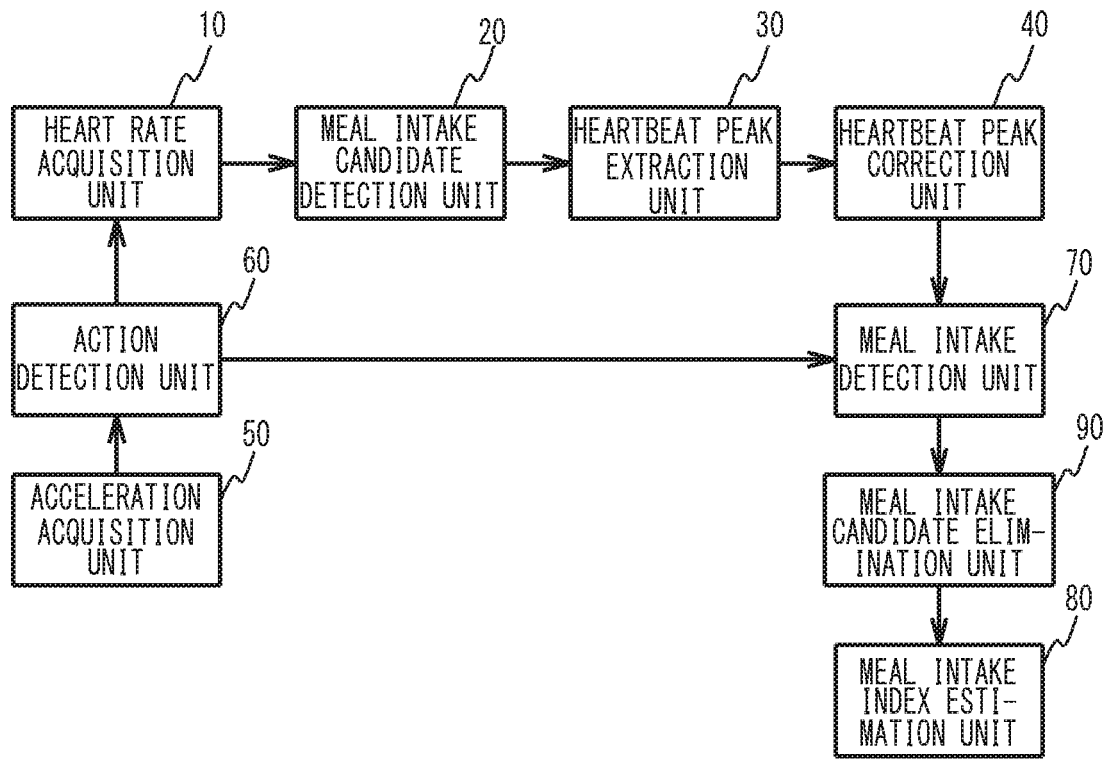
FIG. 9A is a block diagram of functions implemented by the execution of the meal intake detection program.
Figure 9B:
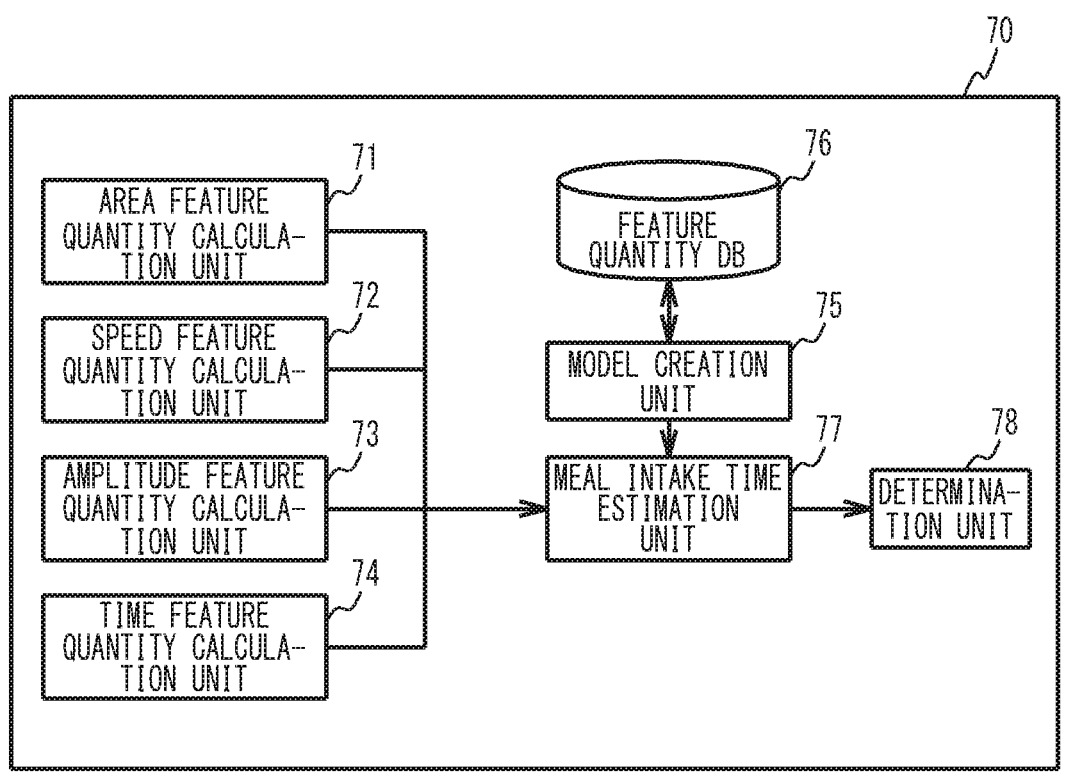
FIG. 9B is a functional block diagram of functions of the meal intake detection unit.

FIG. 9A is a functional block diagram of a meal intake detection device 100a in accordance with a second embodiment. The device structure is the same as that illustrated in FIG. 1A. As illustrated in FIG. 9A, the meal intake candidate elimination unit 90 is newly implemented by the execution of the meal intake detection program of the second embodiment. As illustrated in FIG. 9B, the functional block of the meal intake detection unit 70 is the same as that of FIG. 2B.

The meal intake candidate elimination unit 90 eliminates from candidates the meal intake candidate that is determined as not being a meal intake. This inhibits the meal intake candidate that is determined as not being a meal intake from affecting the heartbeat peaks of other meal intake candidates. Accordingly, the accuracy of the detection of a meal intake and the accuracy of the detection of the index relating to a meal intake are improved.

Figure 11A:
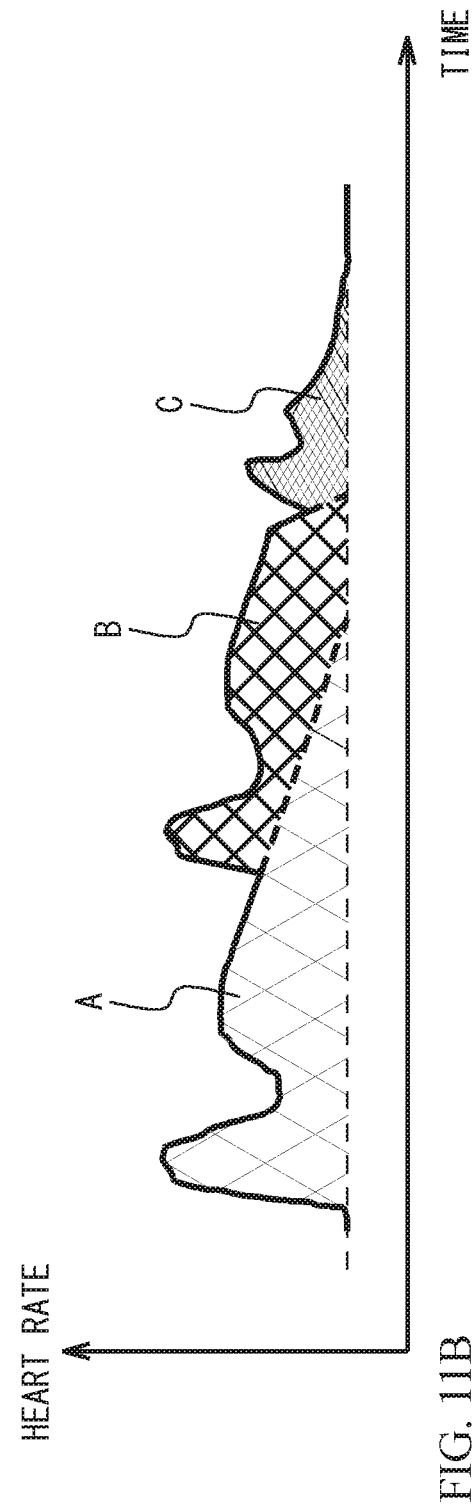
FIG. 11A and FIG. 11B illustrate elimination of a meal intake candidate.
Figure 11B:
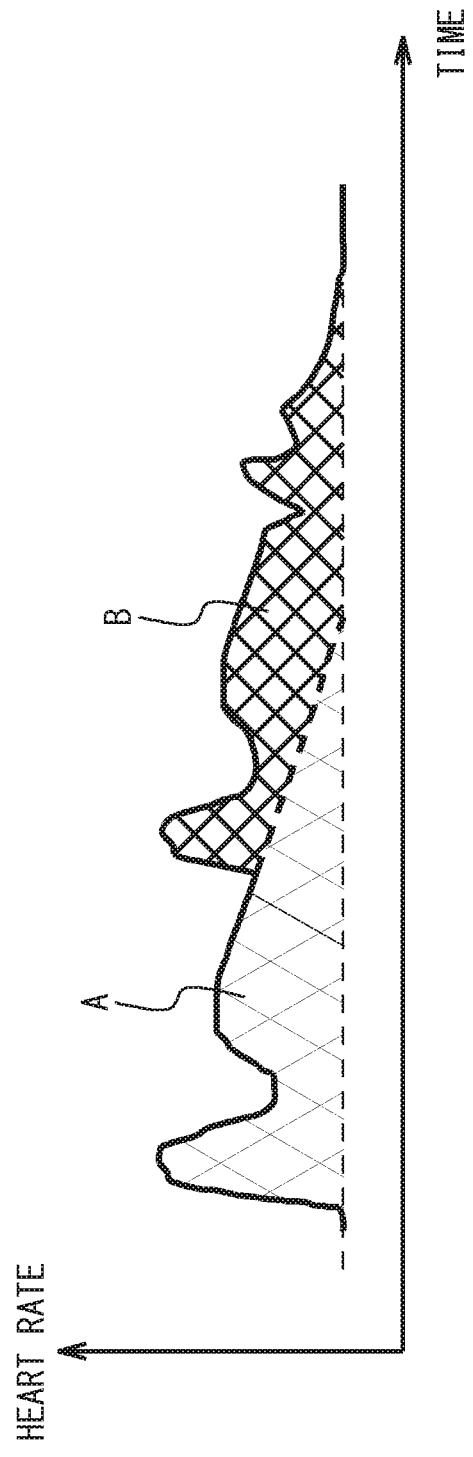

In the temporal changes in heart rate illustrated in FIG. 10, it is assumed that the first meal intake candidate A and the second meal intake candidate B are meal intakes, and the third meal intake candidate C is not a meal intake. In this case, when the third meal intake candidate C is not eliminated from candidates, as illustrated in FIG. 11A, the corrected heartbeat peak of the second meal intake candidate B is affected by the third meal intake candidate C, and the feature vector of the second meal intake candidate B is thereby affected. Thus, as illustrated in FIG. 11B, the elimination of the third meal intake candidate C from meal intake candidates by the meal intake candidate elimination unit 90 eliminates the influence of the third meal intake candidate C, and allows the original heartbeat peak of the second meal intake candidate B to be obtained. Accordingly, the original feature vector of the second meal intake candidate B can be calculated.

Figure 12:
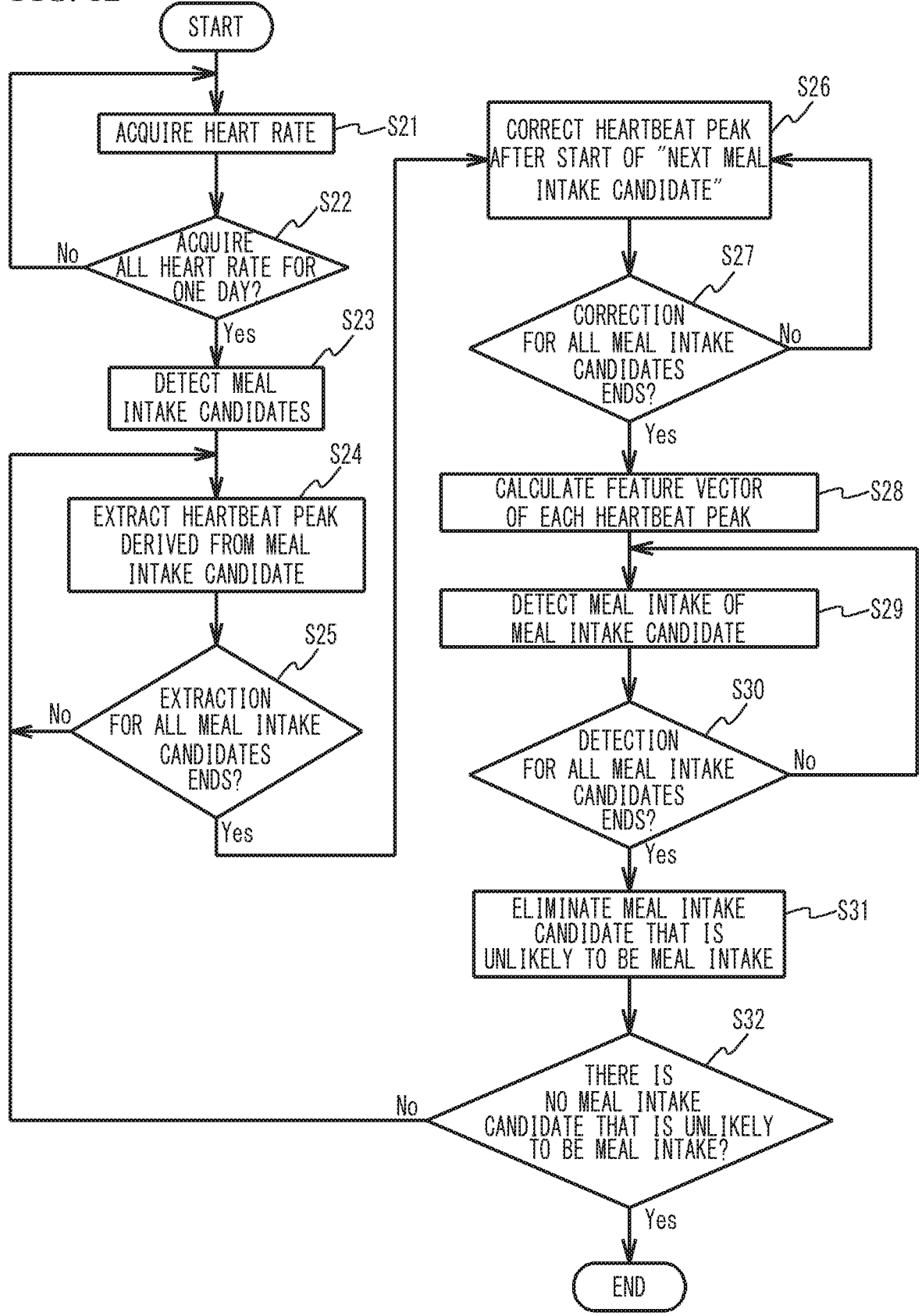
FIG. 12 is a flowchart of a concrete example of a meal intake detection process in accordance with a second embodiment.

FIG. 12 is a flowchart of a concrete example of a meal intake detection process in accordance with the second embodiment. As illustrated in FIG. 12, processes at step S21 through step S25 are the same as those at step S1 through step S5 in FIG. 8. When the determination at step S25 is "Yes", the heartbeat peak correction unit 40 corrects the heartbeat peak after the start of the next meal intake candidate (step S26). At the first execution of step S26, the heartbeat peak after the start of the second meal intake candidate is corrected. Then, the heartbeat peak extraction unit 30 determines whether the heartbeat peaks that need to be corrected are corrected for all the meal intake candidates (step S27). When the determination at step S27 is "No", step S26 is executed again.

When the determination at step S27 is "Yes", the meal intake detection unit 70 calculates the feature vectors of the heartbeat peaks of all the meal intake candidates (step S28). Then, the meal intake detection unit 70 determines whether each meal intake candidate is a meal intake (step S29). Then, the meal intake detection unit 70 determines whether the determination of whether each meal intake candidate is a meal intake has been conducted for all the meal intake candidates (step S30). When the determination at step S30 is "No", step S29 is executed again. When the determination at step S30 is "Yes", the meal intake candidate elimination unit 90 eliminates from candidates the meal intake candidate that is determined as being unlikely to be a meal intake (as not being a meal intake) (step S31). Then, the meal intake candidate elimination unit 90 determines whether there is no meal intake candidate that is determined as not being a meal intake (step S32). When the determination at step S32 is "No", the process is executed again from step S24. Accordingly, the heartbeat peak of each meal intake candidate is extracted again after the meal intake candidate that is determined as not being a meal intake is eliminated from candidates. When the determination at step S32 is "Yes", the execution of the flowchart ends.

In the present embodiment, the meal intake candidate that is determined as not being a meal intake is eliminated from meal intake candidates. Accordingly, the meal intake candidate that is determined as not being a meal intake is inhibited from affecting other meal intake candidates. Therefore, the accuracy of the detection of a meal intake is improved.

(Example of Effects in Real Data)

Figure 13A:
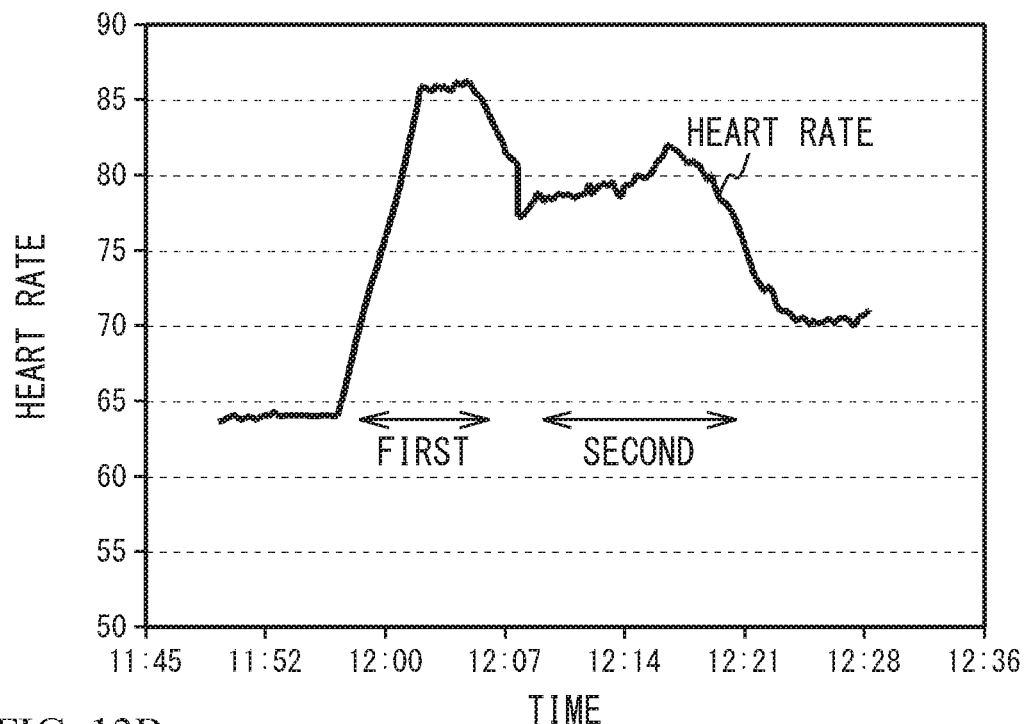
FIG. 13A is real data of temporal changes in heart rate when the interval between two meals was made to be short.

FIG. 13A is measurement data of temporal changes in heart rate when the interval between two meals was made to be short. As an example, the period from the time when the heart rate increases by 10 bpm or more to the time when the heart rate decreases by more than half of the rise is detected as a meal intake. Since the interval between meals is short, the heart rate increase occurring with the second meal intake starts before the heart rate decreases by more than half of the rise of the heart rate. Thus, two meals may be detected as one meal.

Figure 13B:
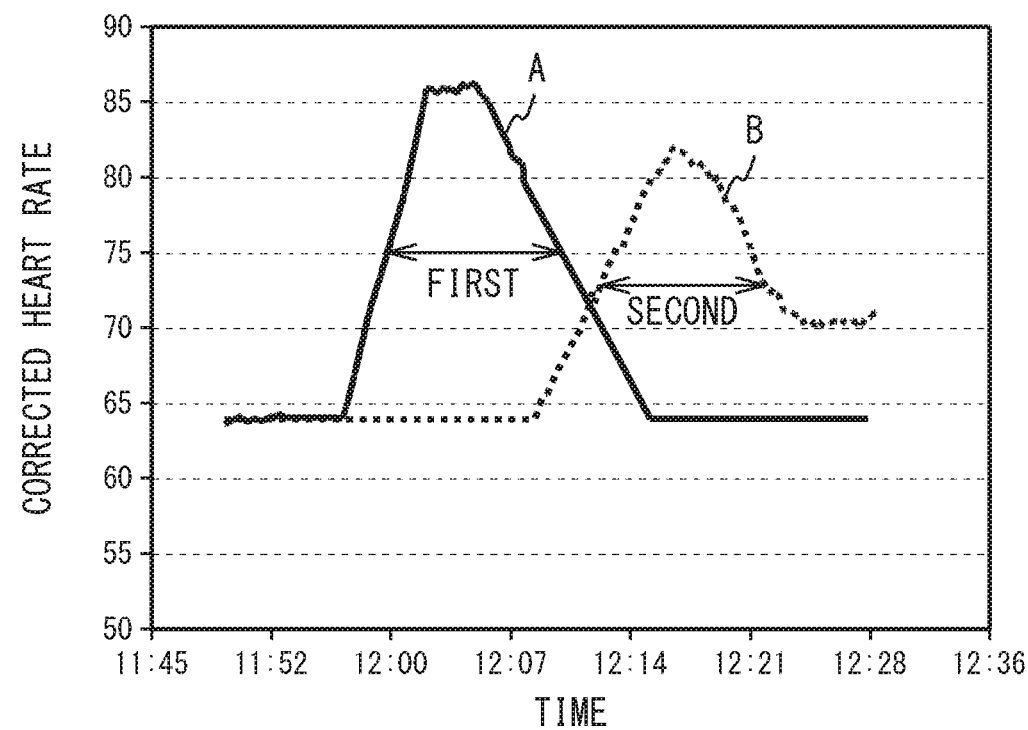
FIG. 13B illustrates separation of meal intake candidates.

FIG. 13B illustrates separation between the first meal intake candidate A and the second meal intake candidate B according to the above embodiments. More specifically, the correction is made under the assumption where the decrease of the heart rate of the first meal intake candidate A continues after the second meal intake candidate B starts.

Such a correction improves the accuracy of the detection of a meal intake for two meal intake candidates.

Figure 14A:
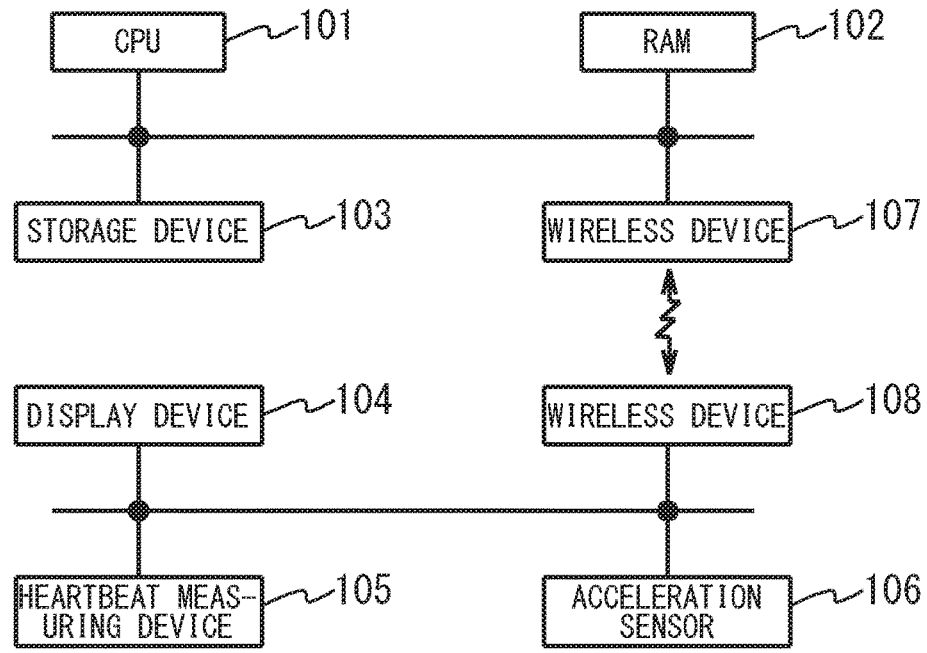
FIG. 14A and FIG. 14B illustrate other device structures of the meal intake detection device.
Figure 14B:
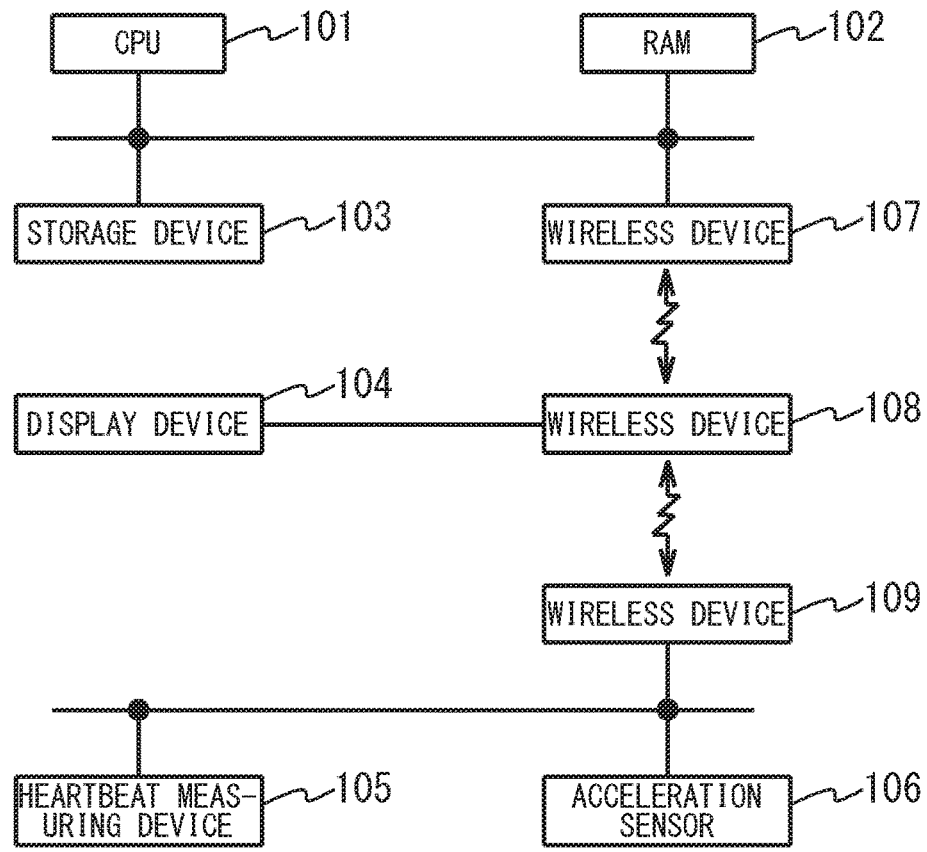

FIG. 14A and FIG. 14B illustrate other device configurations of the meal intake detection device 100 and the meal intake detection device 100a. As illustrated in FIG. 14A, the meal intake detection device may have a configuration in which data is exchanged over radio between a server including: the CPU 101; the RAM 102; the storage device 103; and a wireless device 107 and a wearable device including: the display device 104; the heartbeat measuring device 105; the acceleration sensor 106; and a wireless device 108. Alternatively, as illustrated in FIG. 14B, the meal intake detection device may have a configuration in which data is exchanged over radio among a server including: the CPU 101; the RAM 102; the storage device 103; and the wireless device 107, a terminal including: the display device 104 and the wireless device 108, and a wearable device including: the heartbeat measuring device 105; the acceleration sensor 106; and a wireless device 109.

In the above embodiments, the meal intake candidate detection unit 20 functions as an example of a detection unit that detects a rise at which the ascent rate of the heart rate is equal to or greater than a threshold value. The heartbeat peak extraction unit 30 and the heartbeat peak correction unit 40 function as an example of a separation unit that extracts as a meal intake candidate a time range from a detected rise by the detection unit to the time at which the heart rate decreases to a predetermined value in temporal changes in heart rate, and when the second meal intake candidate is extracted in the extracted time range of the first meal intake candidate, separates the first meal intake candidate and the second meal intake candidate along a predetermined line. The meal intake detection unit 70 functions as an example of another detection unit that detects whether each of the first meal intake candidate and the second meal intake candidate is a meal intake based on feature quantities relating to a meal intake of the separated first meal intake candidate and the separated second meal intake candidate. The meal intake candidate elimination unit 90 functions as an example of an elimination unit that eliminates from meal intake candidates the meal intake candidate that is detected as not being a meal intake by the detection unit among the meal intake candidates extracted by the extraction unit. The meal index estimation unit 80 functions as an example of an estimation unit that estimates an index relating to a meal intake for the meal intake candidate detected as a meal intake by the detection unit.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention.

What is claimed is:

1. A meal intake detection device comprising:
   a memory; and
   a processor coupled to the memory and configured to:
     detect a rise of heart rate,
     extract as a meal intake candidate a time range from a detected rise to time when the heart rate decreases to a predetermined value in temporal changes in heart rate,
     when a second meal intake candidate is extracted in a time range of a first meal intake candidate extracted, separate the first meal intake candidate and the second meal intake candidate along a predetermined line obtained by using the first meal intake candidate to a start point of the second meal intake candidate, and
     detect whether each of the first meal intake candidate and the second meal intake candidate is a meal intake based on feature quantities relating to the first meal intake candidate and the second meal intake candidate that are separated.

2. The meal intake detection device according to claim 1, wherein
   the processor is configured to, when a heart rate of the first meal intake candidate tends to decrease at a time of a rising of the second meal intake candidate, obtain as the predetermined line a line that starts from the time of the rising of the second meal intake candidate and has a slope equal to a slope of heart rate of the first meal intake candidate at the time of the rising of the second meal intake candidate.

3. The meal intake detection device according to claim 1, wherein
   the processor is configured to eliminate from meal intake candidates a meal intake candidate that is detected as not being a meal intake among meal intake candidates extracted.

4. The meal intake detection device according to claim 1, wherein
   the processor is configured to estimate an index relating to a meal intake for a meal intake candidate that is detected as a meal intake.

5. A meal intake detection method implemented by a computer, the meal intake detection method comprising:
   detecting a rise of heart rate;
   extracting as a meal intake candidate a time range from a detected rise to time when heart rate decreases to a predetermined value in temporal changes in the heart rate;
   when a second meal intake candidate is extracted in a time range of a first meal intake candidate extracted, separating the first meal intake candidate and the second meal intake candidate along a predetermined line obtained by using the first meal intake candidate to a start point of the second meal intake candidate; and
   detecting whether each of the first meal intake candidate and the second meal intake candidate is a meal intake based on feature quantities relating to the first meal intake candidate and the second meal intake candidate that are separated.

6. A non-transitory computer readable storage medium storing a meal intake detection program causing a computer to execute a process, the process comprising:
   detecting a rise of heart rate;
   extracting as a meal intake candidate a time range from a detected rise to time when heart rate decreases to a predetermined value in temporal changes in the heart rate;
   when a second meal intake candidate is extracted in a time range of a first meal intake candidate extracted, separating the first meal intake candidate and the second meal intake candidate along a predetermined line obtained by using the first meal intake candidate to a start point of the second meal intake candidate; and detecting whether each of the first meal intake candidate and the second meal intake candidate is a meal intake based on feature quantities relating to the first meal intake candidate and the second meal intake candidate that are separated.

* * * * *